United States Patent [19]

Solow

[11] 4,223,417
[45] Sep. 23, 1980

[54] GLIDING, MECHANIZED TOOTHBRUSH

[76] Inventor: Terry S. Solow, 410 Playa Blvd., La Selva Beach, Calif. 95076

[21] Appl. No.: 8,064

[22] Filed: Jan. 31, 1979

[51] Int. Cl.² .............................................. A46B 13/02
[52] U.S. Cl. .................................. 15/22 R; 15/167 A; 128/62 A
[58] Field of Search .................. 15/22 R, 22 A, 22 C, 15/167 A; 128/62 A

[56] References Cited
U.S. PATENT DOCUMENTS

| Re. 26,589 | 5/1969 | Murov et al. | 15/22 R |
| 2,766,750 | 10/1956 | Darcissac | 128/62 A X |
| 2,771,624 | 11/1956 | Ripper | 15/167 A |
| 3,382,519 | 5/1968 | Piggott | 15/22 R |
| 3,984,890 | 10/1976 | Collis | 15/22 R |
| 4,137,593 | 2/1979 | Porper | 15/167 A |

FOREIGN PATENT DOCUMENTS 2012815 9/1971 Fed. Rep. of Germany ........ 128/62 A

Primary Examiner—Edward L. Roberts
Attorney, Agent, or Firm—Robert G. Slick

[57] ABSTRACT

A Gliding, Mechanized Toothbrush is provided wherein a small box-like member, called the head, having a handle thereon, encloses a pair of brushes adapted to brush both sides of a tooth at the same time. The bristles of these brushes extend at an angle to the sides of the teeth whereby these bristles also enter and clean the sulcus area and embrasures. In the preferred embodiment of this invention, additional brushes clean the biting surfaces of the teeth. A handle is used to pull the head along a row of teeth. Preferably, the head is mounted on a swivel so that the head can be turned relative to the handle, facilitating brushing teeth in various parts of the mouth.

18 Claims, 16 Drawing Figures

GLIDING, MECHANIZED TOOTHBRUSH

SUMMARY OF THE INVENTION

The present invention relates to a gliding, mechanized toothbrush wherein the plurality of mechanically-driven brush elements are mounted in a head in such a manner that the brush elements can be passed over a row of teeth, brushing both sides of the tooth at the same time as well as the top of the tooth. The angle that the bristles of the brushes come down on each side of a tooth is chosen to be an acute angle, so that the bristles also enter and clean the sulcus area and embrasures. The brushes are made to vibrate in a "jackhammer" fashion so that the bristles vibrate back and forth along their axes. This vibratory mode for the bristles is important for the efficient cleaning of the sulcus areas, the embrasures and the teeth. The bristles are chosen to be soft, pliable and bendable, yet still resilient enough to clean accumulated plaque and not harm the gum tissues or the teeth.

In accordance with one embodiment of the invention, the head contains a pair of brushes and, in accordance with other embodiments of the invention, three or more brushes may be employed.

Various mechanical means can be employed to actuate the brushes, such as vibrating rods or strings or reciprocating cams or gears, but preferably this is accomplished by means of a flexible tube leading to a source of alternating vacuum and pressure.

The brushes proper are mounted in a head, and this head is preferably rotatably mounted on a handle. Thus, as is later explained in detail, the relative angular position of the head and handle in the preferred embodiment can be altered for various parts of the mouth. This may involve a free-moving swivel connection or a snap-type connection wherein a detent locks the head into either one of two positions with respect to the handle. Additional positions may also be incorporated.

In a less preferred embodiment, the handle is fixed relative to the head and is not rotatable.

The handle itself can also serve as the means for powering the brushes. For instance, the handle may be hollow and connected through a tube to an alternating source of vacuum and pressure for the purpose of actuating the brush elements.

The swivel arrangement wherein the head can turn with respect to the handle greatly facilitates the brushing operation as is later explained in detail. Preferably, the head has rollers or glides thereon which tend to guide the head over the row of teeth.

Thus, the primary object of the present invention is to provide a mechanized toothbrush having a relatively small, compact head wherein both sides and the top of a tooth are brushed at the same time by mechanical means and wherein the bristles also do a good cleaning job on the embrasures as well as entering and cleaning the sulcus area.

Various other features and advantages of the invention will be brought out in the balance of the specification.

DESCRIPTION OF THE PREFERRED EMBODIMENTS

Figure 1:
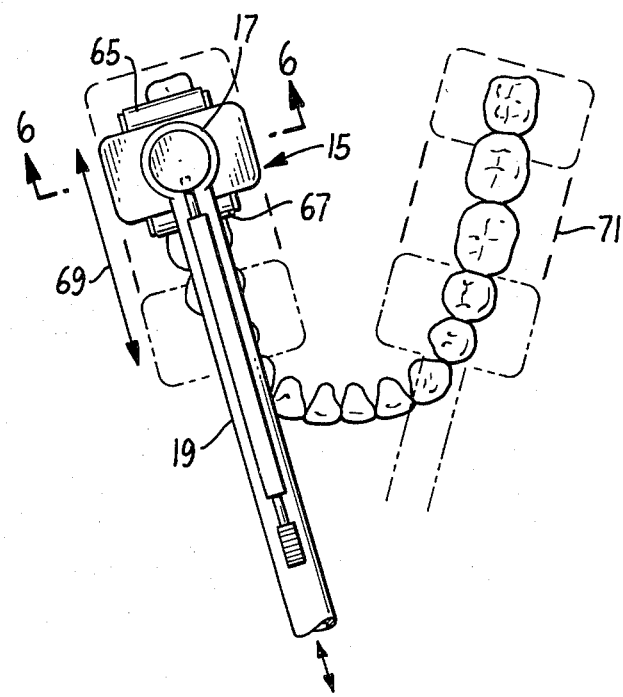
FIG. 1 is a plan view of a toothbrush embodying the present invention showing its use in brushing the molars and the bicuspids.
Figure 2:
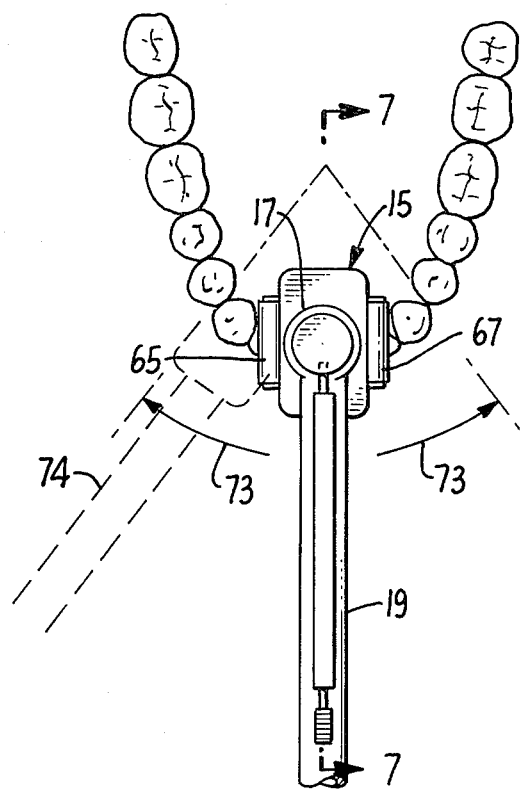
FIG. 2 is a view, similar to FIG. 1, showing the brush in use for brushing the incisors and the canines.

Referring now to the drawings shown in FIGS. 1 and 2, the toothbrush of the present invention includes a head, generally designated 15, connected by a swivel arrangement 17 to a handle 19. In the preferred embodiments the head 15 can rotate with respect to the handle 19 via swivel 17 for reasons later brought out in detail; and in FIGS. 1, 2, 4 and 5, the relative position of the head and handle is held in a desired angular relationship by way of a detent means. This detent means is not mandatory and, in the embodiment shown in FIG. 3, the head 21 is free to rotate with respect to handle 23 via swivel 20 and the teeth themselves will guide the head 21 in the correct angular relationship as will be brought out later in detail.

Figure 4:
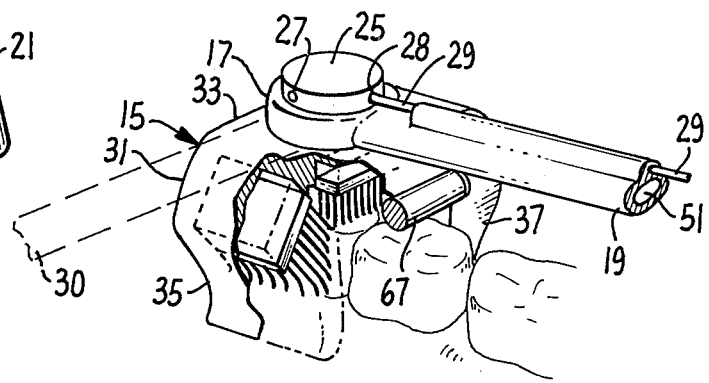
FIG. 4 is an enlarged perspective view of the brush head.

In the preferred embodiment of this invention, it is desired to provide means for holding the head in either one of two positions, 90° apart in relation to the handle. FIG. 1 shows the head 15 perpendicular to handle 19 and FIG. 2 shows head 15 shifted 90° so that it is parallel to handle 19. FIG. 4 shows a perspective view showing handle 19 in a similar position to that shown in FIG. 1. Handle 30 (dashed lines) of FIG. 4 shows the other 90° position, similar to handle 19 versus body 15 of FIG. 2.

Figure 5:
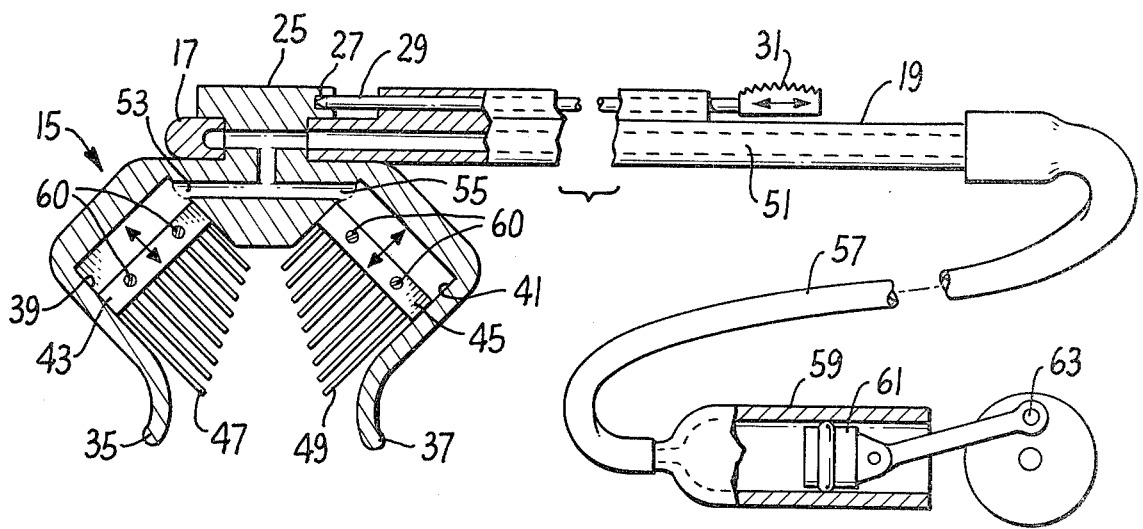
FIG. 5 is a side view, partially in section, showing one form of actuating mechanism for the brushes.

As best seen in FIGS. 4 and 5, head 15 is provided with a top cap 25, which mates with swivel 17. Cap 25 has two depressions 27 and 28 that are 90° apart. The handle 19 is provided with a detent pin 29, which can be moved in and out by means of handle 31, so that one can pull back on handle 31, turn the head 15 to a desired position, and push back on handle 31 to lock the head in a desired position with respect to the handle. Alternatively, the pin 29 could be spring-loaded, and the depressions 27 and 28 made shallow so that the head could be turned to a desired position, and the detent would then snap into one of the two depressions 27 or 28 and hold it in that position. Additional depressions may be provided at other angles if desired.

The head 15 has a casing 31 which includes the top 33 and sides 35 and 37 which extend downwardly so that the sides substantially encompass all the tooth and a portion of the gum. Within the head 15 are the individual brush elements and ordinarily two to eight brushes would be employed, depending on the required cost of manufacture and the desired speed and brushing efficiency of the final toothbrush design.

Various methods can be used for actuating the individual brush elements but a preferred method is a pneumatic method as is best seen in FIG. 5. Here the head 15 is shaped to provide two chamber walls 39 and 41 and each of the chambers has a piston forming a tight fit with the chamber walls and being adapted to move back and forth therein. Each of the pistons has a brush 43 and 45 attached to it by screws 60. Brushes 43 and 45 have bristle elements 47 and 49 firmly embedded. Brushes 43 and 45 are easily replaceable, via screws 60, by the user whenever wear or other reasons dictate.

Although it is not mandatory, the head 15 can be provided with rollers 65 and 67 shown in FIGS. 1 and 2 that maintain the head and its reciprocating brushes at a fixed height above the tops or biting surfaces of the teeth. Smooth gliding surfaces may be substituted for the rollers where lower manufacturing costs are required.

Referring to FIG. 5, handle 19 is hollow and has a passage 51 therein, and this leads to the passages 53 and 55 which connect passage 51 to the head space above the pistons 43 and 45. Passage 51 leads to a flexible tube 57 connected to a cylinder 59 having a piston 61 therein driven in the usual manner by the crank 63. With the arrangement shown, it is obvious that reciprocation of the piston 61 will result in alternating vacuum and air pressure in the space above the pistons 43 and 45, causing them to move up and down. Hydraulic pressure can be substituted for the pneumatic operation shown.

Figure 3:
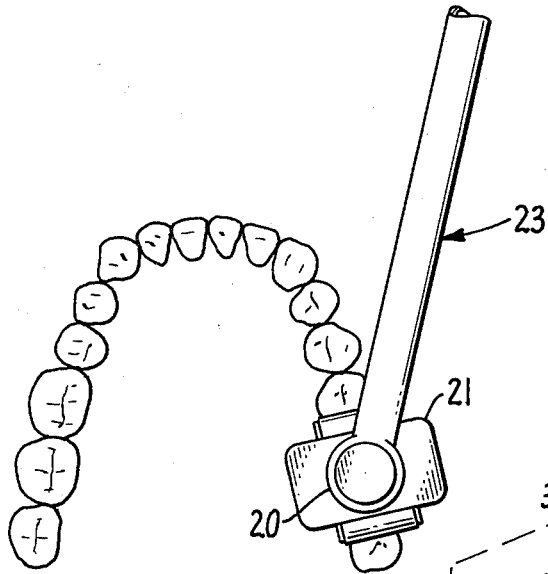
FIG. 3 is a plan view of another brush wherein the head is free to rotate with respect to the handle.

The arrangement shown in FIG. 3 can be the same except that here the detent or snap arrangement is missing so that the head can rotate freely with respect to the handle. This, in effect, makes the device self-centering.

The method of using the Gliding, Mechanized Toothbrush will now be described. One first turns the head 17 at right angles to the handle 19 as is shown in FIG. 1. As can be seen, the molars and bicuspids are in a substantially straight line. One places the brush over the molars, as is shown on the left hand side of FIG. 1, turns on the power, and then moves the brush back and forth over the molars and bicuspids as indicated by the arrow 69. One now moves the head to the opposite side of the dental arch, as is shown by dashed lines 71 on the right hand side of FIG. 1 and repeats the operation with these molars and bicuspids. Now one inverts the brush and runs it over the upper molars and bicuspids of the upper dental arch in a similar manner.

One now rotates the head 15 (90°) so it is in line with the handle 19 as is shown in FIG. 2. The brush is placed over the incisors and moved back and forth through an arc covering the canines and the incisors as is indicated by the arrow 73. In a similar fashion, after the lower canines and incisors are cleaned, the toothbrush is turned over for cleaning the upper canines and incisors. Of course, if the embodiment shown in FIG. 3 is employed, it is not necessary to rotate head 21 manually but as the teeth are brushed, the head will naturally follow the contour of the teeth and rotate with respect to the handle 23 automatically.

Figure 6:
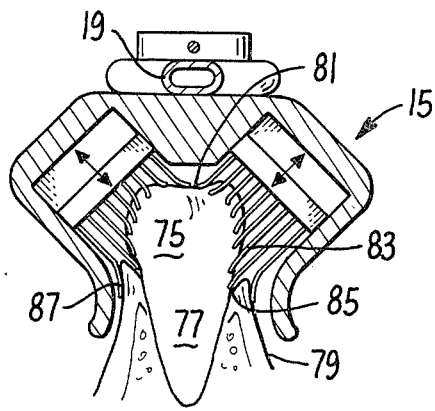
FIG. 6 is a sectional view on the line 6—6 of FIG. 1 showing the action of the brushes on a molar.
Figure 7:
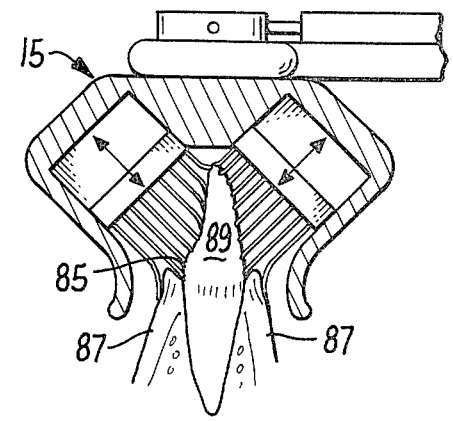
FIG. 7 is a sectional view showing the action of the brushes on an incisor.

The action of the toothbrush is shown on various types of teeth in FIGS. 6 and 7. In FIG. 6 a molar having a crown 75 and a root 77 bounded by gum 79 is shown and the head 15 has been rotated so that it is perpendicular to the handle 19, i.e. similar to that shown in FIG. 1. It will be seen that the bristles do a thorough job of brushing both the top flat surface 81, the sides 83, as well as the important sulcus area 85, and that the bristles also massage the gum as is shown at 87.

In FIG. 7, head 15 has been turned 90° so that it is now parallel to handle 19. This position is similar to that shown in FIG. 2 and is here shown brushing an incisor 89. As before, it will be seen that all of the surfaces of the tooth are thoroughly brushed including the sulcus 85. The gum 87 is gently massaged.

Figure 8:
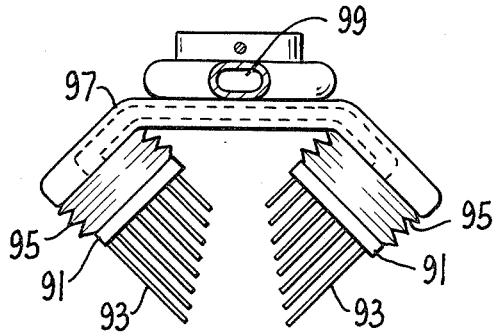
FIG. 8 is a sectional view showing a bellows arrangement for driving the brushes.

Various methods can be used to actuate the brush elements and another embodiment of the invention is shown in FIG. 8 wherein the backing 91 for the bristles 93 is connected by means of a bellows 95 to a head 97. Tube 99 leads to a source of alternating vacuum and pressure, driving the bristles as previously described.

Figure 9:
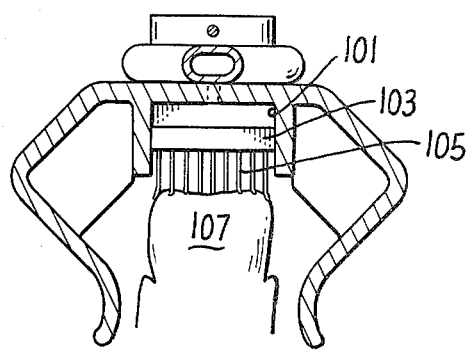
FIG. 9 is a sectional view showing an embodiment of the invention wherein a separate brush is used for the top or biting surfaces of the teeth. To simplify the illustration, the side brushes are not shown.

Ordinarily, when trying to keep the toothbrush cost low, it will suffice to use only one pair of brushes with a brush on each side, since these bristles can be caused to clean even the top surface of a molar as is shown in FIG. 6 as well as the sides. However, it is more desirable to provide a third or top brush as is shown in FIG. 9 to clean the top surfaces of the teeth in a faster and more efficient manner. Here the side brushes are not illustrated since they are as previously described. This top brush may be chosen to be in the same plane as the side brushes and designed to reciprocate in-phase or 180° out-of-phase with these side brushes.

A simpler approach is to make this top brush narrow and place it so that it is not in the same plane with the side brushes. FIGS. 10, 11, 12 and 14 show this approach with the top brush shown singly (110) and in pairs (44 and 46). Being in different operating planes, any and all brushes can be shaped as desired without interfering with any other brush.

In forthcoming description of FIGS. 10, 11, 12 and 14, all side brushes when viewed in cross section have their bristles striking the tooth and sulcus areas at an acute angle to the tooth, similar to that shown in FIGS. 6 and 7.

Figure 10:
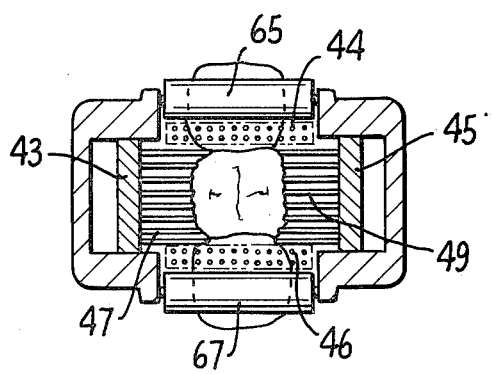
FIG. 10 is a plan view in section of a brush head showing a pair of brushes whose bristles brush both sides of a tooth and two narrow brushes that brush the biting surfaces of the teeth.

FIG. 10 shows a sectional view through a brush head. It will be seen that bristles 47 and 49 of brushes 43 and 45 brush the sides of the molar as well as entering the embrasures between the teeth. Brushes 44 and 46 brush the tops or biting surfaces of the teeth.

Figure 11:
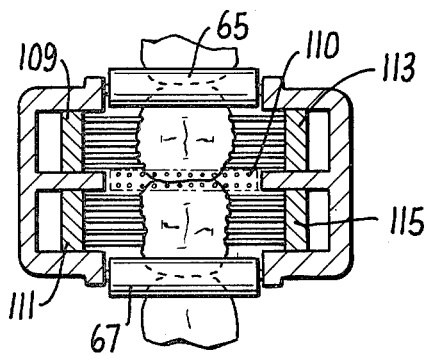
FIG. 11 is a plan view in section wherein the side brushes are split into double pairs and the bristles of these brushes brush both sides of the teeth. In addition, a narrow brush brushes the tops of the teeth.

FIG. 11 is a similar plan view showing another embodiment of the invention wherein pairs of brushes are used on each side of the teeth; thus, this Figure shows the brushes 109 and 111 on one side of the teeth, while brushes 113 and 115 are on the opposite side. A single brush 110 brushes the tops of the teeth. This embodiment is particularly effective in keeping the toothbrush centered over the teeth as a train is centered over the tracks if the pairs of brushes are driven alternately rather than in synchronism (i.e., 180° out of phase). This is so because there is much less leeway for the head to wander from the desired center position over the teeth because when brush pair 111 and 115 release their grab on the teeth, brushes 109 and 113 apply their grab, etc.

Figure 12:
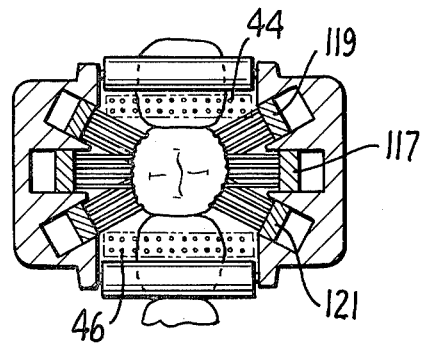
FIG. 12 is a plan view in section of a brush head wherein three sets of brushes are used on each side of a tooth for better cleaning action in the embrasures and sulcus. In addition, two narrow brushes brush the biting surfaces of the teeth.

In FIG. 12, another embodiment of the invention is shown wherein a set of three brushes is used on each side of the teeth. This embodiment also shows that the brushes can be set at various angles around the tooth. Thus, looking at the brushes on one side, the brush 117 is set at the side of the tooth while the brushes 119 and 121 are set at an angle. This is particularly effective in entering the embrasures and sulcus areas. The brushes on the opposite side are obviously a mirror image and are not described in detail.

Figure 13:
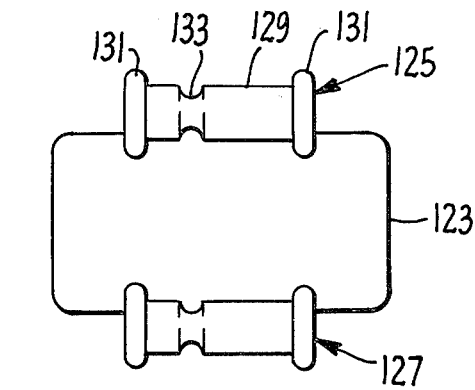
FIG. 13 is a diagrammatic plan view showing an alternate form of guiding the roller.

In FIG. 13, a diagrammatic view is shown of a head 123 having guiding rollers, generally designated 125 and 127. The guiding rollers have a central flat portion 129 which glides over the surfaces of the teeth, while the rims 131 on the rollers keep the rollers from sliding off the molars and bicuspids. The notches 133 in the rollers aid in centering the brush heads over the incisors and the canines.

Figure 14:
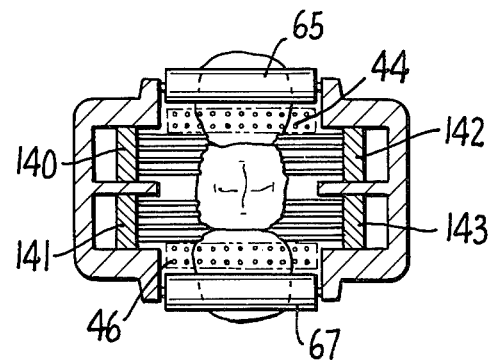
FIG. 14 is a plan view in section wherein the side brushes are split into double pairs and the bristles of these brushes brush both sides of the teeth. In addition, two narrow brushes brush the biting surfaces of the teeth.

FIG. 14 is another embodiment of the invention similar to FIG. 11 but with paired, top brushes versus a single top brush in FIG. 11. In this embodiment, side brushes 140, 141, 142 and 143 are employed with top brushes 44 and 46.

Figure 15:
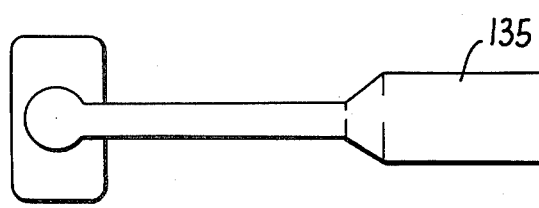
FIG. 15 is a plan view of an electrically motor-driven toothbrush having a built-in rechargeable battery.

Although the Mechanical, Gliding Toothbrush of the present invention is preferably pneumatically operated, it is also possible to operate it in other manners. In the embodiment shown in FIG. 15, a handle 135 encloses a driving motor and rechargeable battery, and prongs 137 enable one to plug into an outlet for recharging the battery. Said motor could drive crank 63 of FIG. 5 where hollow handle 19 could attach directly to cylinder 59 so that the system of FIG. 5 is built into the outline of FIG. 15. Other well known reciprocating systems may be built into the outline of FIG. 15, such as vibrating rods and strings or reciprocating cams or gears (not shown).

Figure 16:
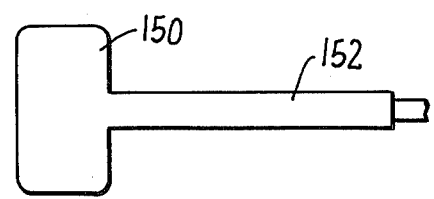
FIG. 16 is a plan view of a brush wherein the relative positions of the head and handle are fixed.

Although it is preferred that the head be rotatable with respect to the handle, this is not strictly necessary. Thus, in FIG. 16, head 150 is fixed with respect to handle 152. In this case, the user would brush his molars and bicuspids as shown in FIG. 1. To brush the incisors and canines, the user simply would turn the toothbrush handle manually, thereby rotating the head into the proper position.

Ordinarily, it is not necessary to provide any means for adjusting the position of the piston-chambers or other means for holding the brushes, since usually sufficient movement or throw is imparted to the brushes to clean anything from the largest to the smallest tooth, as is shown in FIGS. 6 and 7. However, in some instances, it is desirable to provide for such an adjustment so that the brushes are set farther apart for a molar and closer together for a small tooth such as an incisor. This is easily achieved by means of a cam or gear arrangement, so that as the head is turned 90° relative to the handle, the piston-chambers are brought nearer or farther apart. Refer to FIGS. 1 and 2.

Although certain specific embodiments of the invention have been shown, these are for illustrative purposes only and many variations can be made of the structures shown without departing from the spirit of this invention.

I claim:

1. A mechanized toothbrush for cleaning both sides of a tooth simultaneously, said toothbrush having a housing adapted to be moved along a row of teeth comprising a head portion and a handle portion, said head portion containing a pair of brushes, each of said brushes being individually movable with respect to said head, said brushes having bristles set at an acute angle to the sides of the tooth, pointing toward the sulcus, said brushes being adapted to move toward and away from each other during vibration, said brushes being adapted to contact opposite sides of the tooth, and means to vibrate said brushes to contact and clean opposite sides of a tooth simultaneously.

2. The toothbrush of claim 1 where said head has glide means so that said head can be moved along a row of teeth.

3. The toothbrush of claim 2 wherein said head has rollers, said rollers being adapted to roll over the tops of the teeth.

4. The toothbrush of claim 3 wherein said rollers have lips at the edge thereof to prevent said rollers from sliding off the teeth.

5. The toothbrush of claim 3 wherein said rollers have notches therein, said notches locating said rollers over the incisors and bicuspids.

6. The structure of claim 2 wherein the brushes are caused to vibrate in a direction parallel to the bristles.

7. The toothbrush of claim 1 where there is connection means between said head and said handle, whereby the angle between the head and the handle can be altered.

8. The toothbrush of claim 1 having at least one additional brush adapted to clean the top or biting surface of a tooth, said brush being adapted to be movable in said head, said brush being adapted to move toward and away from the tooth top during vibration, said brush being adapted to contact the top of the tooth, and means to vibrate said brush to clean the top of the tooth.

9. The toothbrush of claim 1 having detent means between said head and said handle, whereby said head can be turned to a desired angle with respect to said handle and maintained in this desired angular relationship.

10. The toothbrush of claim 1 wherein the head has more than two brushes normally consisting of an equal number on each side of a tooth, said brushes being adapted to be driven in any selected phase relationship with each other.

11. The toothbrush of claim 10 wherein said brushes have bristles adapted to impinge on a tooth's surface at different selected angles for optimum cleaning and embrasure penetration.

12. The toothbrush of claim 11 wherein there is added at least one brush to clean the top of the tooth.

13. The toothbrush of claim 10 wherein there is added at least one brush to clean the top of the tooth.

14. The structure of claim 1 wherein the brushes are caused to vibrate in a plane parallel to the bristles.

15. The structure of claim 1 wherein said pair of brushes brush the sides and top of a tooth at the same time.

16. The structure of claim 15 where said head has glide means so that the head can be moved along a row of teeth.

17. The structure of claim 1 wherein the means to vibrate the bristles is pneumatic.

18. The structure of claim 1 wherein the means to vibrate the bristles is hydraulic.